(12) United States Patent
Wang et al.

(10) Patent No.: US 10,932,481 B2
(45) Date of Patent: Mar. 2, 2021

(54) THERMOSTABLE PROTEASE AND METHODS OF MAKING AND USING THE SAME

(71) Applicant: BioResource International, Durham, NC (US)

(72) Inventors: Jeng-Jie Wang, Durham, NC (US); Sanjeewa Rupasinghe, Durham, NC (US)

(73) Assignee: BioResource International, Inc., Durham, NC (US)

( * ) Notice: Subject to any disclaimer, the term of this patent is extended or adjusted under 35 U.S.C. 154(b) by 0 days.

(21) Appl. No.: 16/169,462

(22) Filed: Oct. 24, 2018

(65) Prior Publication Data

US 2019/0045813 A1 Feb. 14, 2019

Related U.S. Application Data

(63) Continuation of application No. PCT/US2017/029628, filed on Apr. 26, 2017.

(60) Provisional application No. 62/328,051, filed on Apr. 27, 2016.

(51) Int. Cl.

| | |
|---|---|
| *C12N 9/54* | (2006.01) |
| *C12N 15/52* | (2006.01) |
| *C12N 1/20* | (2006.01) |
| *A23K 20/189* | (2016.01) |
| *A23K 20/174* | (2016.01) |
| *A23K 50/75* | (2016.01) |
| *A23K 50/30* | (2016.01) |
| *A23K 20/20* | (2016.01) |
| *A23K 10/14* | (2016.01) |

(Continued)

(52) U.S. Cl.
CPC ............ *A23K 20/189* (2016.05); *A23K 10/14* (2016.05); *A23K 20/174* (2016.05); *A23K 20/30* (2016.05); *A23K 50/30* (2016.05); *A23K 50/75* (2016.05); *C12N 1/20* (2013.01); *C12N 9/54* (2013.01); *C12N 15/111* (2013.01); *C12N 15/52* (2013.01); *C12N 15/62* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,712,147 A | 1/1998 | Shih et al. | |
| 2015/0259662 A1* | 9/2015 | Stringer | C12N 9/485 426/63 |
| 2019/0045813 A1* | 2/2019 | Wang | A23K 10/14 |

FOREIGN PATENT DOCUMENTS

| | | |
|---|---|---|
| CN | 102936588 A | 2/2013 |
| CN | 103602653 A | 2/2014 |

OTHER PUBLICATIONS

PIR Accession No. G83756, published Dec. 1, 2000 (Year: 2000).*

(Continued)

*Primary Examiner* — Richard C Ekstrom
(74) *Attorney, Agent, or Firm* — NK Patent Law

(57) ABSTRACT

Proteolytic enzyme variants that exhibit improved thermal stability relative to the wild type protease *Bacillus licheniformis* PWD-1 protease kerA are provided. The protease variants are derived by the mutation of at least one amino acid residue of the mature *Bacillus licheniformis* PWD-1 protease kerA. The variant proteases are useful as animal feed additives to improve the digestibility and/or the nutritional value of the animal feed.

22 Claims, 3 Drawing Sheets

Specification includes a Sequence Listing.

(51) Int. Cl.
*C12N 15/11* (2006.01)
*C12N 15/62* (2006.01)

(56) References Cited

OTHER PUBLICATIONS

UniProt Accession No. A0A0M5JLX4_9BACI, published Dec. 9, 2015 (Year: 2015).*
GenBank Accession No. KRT93153.1, published Nov. 16, 2015 (Year: 2015).*
GenBank Accession No. WP_026586291.1, published Jun. 11, 2014 (Year: 2014).*
WIPO; International Search Report for International Application No. PCT/US17/29628 dated Aug. 8, 2017.
WIPO; Written Opinion for International Application No. PCT/US17/29628 dated Aug. 8, 2017.
Liu, Baihong et al., "Enhanced thermostability of keratinase by computational design and empirical mutation", Journal of Industrial Microbiology & Biotechnology, Epub. Apr. 26, 2013, vol. 40, pp. 697-704.
Fang, Zhen et al., "Enhancement of the catalytic efficiency and thermostability of *Stenotrophonas* sp. keratinase KerSMD by domain exchange with KerSMF", Microbial Biotechnology, Jan. 2016, vol. 9, No. 1, pp. 35-46.
NCBI, GenBank accession No. AAS86761.1, Apr. 13, 2004.
PCT, International Preliminary Report on Patentability for PCT/US2017/029628, dated Oct. 30, 2018.
EPO; Extended European Search Report for European Patent Application No. 17790341.6 dated Nov. 21, 2019, 7 pages.
Martinez, Ronny, et al., "Increasing activity and thermal resistance of Bacillus gibsonii alkaline protease (BgAP) by directed evolution", Biotechnology and Bioengineering, vol. 110, No. 3, Nov. 1, 2012, pp. 711-920.
Huiman, Zhao, et al., "Directed evolution converts subtilisin E into a functional equivalent of thermitase", Protein Engineering, Oxford University Press, Surrey, GB, vol. 12, No. 1, Jan. 1, 1999, pp. 47-53.

* cited by examiner

SEQUENCE LISTING

```
<160> NUMBER OF SEQ ID NOS: 29

<210> SEQ ID NO 1
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205
```

-continued

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
            245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Pro Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Ser Gly Thr Ser Met Val Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Asp Ser Phe Tyr Tyr Gly
            355                 360                 365

Lys Gly Leu Ile Asn Val Glu Ala Ala Ala Gln
            370                 375

<210> SEQ ID NO 2
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
        210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
        370                 375

<210> SEQ ID NO 3
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val

```
                165                 170                 175
Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Ser Met Asp
    210                 215                 220

Val Ile Asn Met Ser Leu Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Cys Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
    370                 375

<210> SEQ ID NO 4
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140
```

Glu Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Pro Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Asp Ser Phe Tyr Tyr Gly
        355                 360                 365

Lys Gly Leu Ile Asn Val Glu Ala Ala Ala Gln
    370                 375

<210> SEQ ID NO 5
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

```
Ala Asn Val Lys Val Ala Val Leu Asp Thr Gly Ile Gln Ala Ser His
            130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                    165                 170                 175

Ala Ala Leu Asp Asn Thr Thr Gly Val Leu Gly Val Ala Pro Ser Val
                180                 185                 190

Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                    245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                    325                 330                 335

Leu Ile Leu Ser Lys His Pro Asn Leu Ser Ala Ser Gln Val Arg Asn
                340                 345                 350

Arg Leu Ser Ser Thr Ala Thr Tyr Leu Gly Asp Ser Phe Tyr Tyr Gly
            355                 360                 365

Lys Gly Leu Ile Asn Val Glu Ala Ala Ala Gln
        370                 375

<210> SEQ ID NO 6
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
```

```
                100                 105                 110
Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
        130                 135                 140

Glu Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
    370                 375

<210> SEQ ID NO 7
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80
```

Lys Glu Ala Leu Lys Glu Val Lys Asn Asp Pro Asp Val Ala Tyr Val
            85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
        130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Cys Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Ser Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
        370                 375

```
<210> SEQ ID NO 8
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8
```

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
            85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
    130                 135                 140

Glu Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Pro Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Asp Ser Phe Tyr Tyr Gly
        355                 360                 365

Lys Gly Leu Ile Asn Val Glu Ala Ala Ala Gln
    370                 375

<210> SEQ ID NO 9
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 9

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val 35                  40                  45
Lys Thr Ala Ser Val Lys Lys Asp Ile Ile Lys Glu Ser Gly Gly Lys
 50                  55                  60

Val Asp Lys Gln Phe Arg Ile Ile Asn Ala Ala Lys Ala Lys Leu Asp
 65                  70                  75                  80

Lys Glu Ala Leu Lys Glu Val Lys Asn Asp Pro Asp Val Ala Tyr Val
                 85                  90                  95

Glu Glu Asp His Val Ala His Ala Leu Ala Gln Thr Val Pro Tyr Gly
                100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
        130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala Ala
                245                 250                 255

Ala Gly Asn Ser Gly Ser Ser Gly Cys Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
        370                 375

<210> SEQ ID NO 10
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Ser Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Cys Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Gln
    370                 375

<210> SEQ ID NO 11
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
            35                  40                  45

Lys Thr Ala Ser Val Lys Asp Ile Ile Lys Glu Ser Gly Gly Lys
50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
            85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
            130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
            165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Ser Met Asp
            210                 215                 220

Val Ile Tyr Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
            245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
            290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
            325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
            355                 360                 365

Lys Gly Leu Ile Asn Val Glu Ala Ala Ala Gln
    370                 375

<210> SEQ ID NO 12
<211> LENGTH: 379
<212> TYPE: PRT
<213> ORGANISM: Artificial Sequence
<220> FEATURE:

<223> OTHER INFORMATION: Description of Artificial Sequence: Synthetic
       construct

<400> SEQUENCE: 12

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Cys Thr Asn Thr Ile Arg Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Gln
    370                 375

<210> SEQ ID NO 13

<211> LENGTH: 379
<212> TYPE: PRT
<213> ORGANISM: Artificial Sequence
<220> FEATURE:
<223> OTHER INFORMATION: Description of Artificial Sequence: Synthetic construct

<400> SEQUENCE: 13

Met Met Arg Lys Lys Ser Phe Trp Leu Gly Met Leu Thr Ala Phe
1               5                   10                  15

Leu Val Phe Thr Met Ala Phe Ser Asp Ser Ala Ser Ala Gln Pro
                20                  25                  30

Ala Lys Asn Val Glu Lys Asp Tyr Ile Val Gly Phe Lys Ser Val
                35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
                100                 105                 110

Ile Pro Leu Ile Lys Ala Asp Lys Val Gln Ala Gln Gly Phe Lys Gly
                115                 120                 125

Ala Asn Val Lys Val Ala Val Leu Asp Thr Gly Ile Gln Ala Ser His
                130                 135                 140

Glu Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
                180                 185                 190

Ser Leu Tyr Ala Val Lys Val Leu Asn Ser Ser Gly Ser Gly Ser Tyr
                195                 200                 205

Ser Gly Ile Val Ser Gly Ile Glu Trp Ala Thr Thr Asn Gly Met Asp
210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
                275                 280                 285

Asn Arg Ala Ser Phe Ser Ser Val Gly Ala Glu Leu Glu Val Met Ala
                290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
                340                 345                 350

Arg Leu Ser Ser Thr Ala Thr Tyr Leu Gly Asp Ser Phe Tyr Tyr Gly
                355                 360                 365

Lys Gly Leu Ile Asn Val Glu Ala Ala Ala Gln

```
                370                 375

<210> SEQ ID NO 14
<211> LENGTH: 379
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Ser Met Asp
    210                 215                 220

Val Ile Tyr Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Cys Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Pro Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350
```

```
Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
        370                 375
```

<210> SEQ ID NO 15
<211> LENGTH: 1140
<212> TYPE: DNA
<213> ORGANISM: Artificial Sequence
<220> FEATURE:
<223> OTHER INFORMATION: Description of Artificial Sequence: Synthetic construct

<400> SEQUENCE: 15

```
atgatgagga aaagagtttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaggacat catcaaagag      180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt ggggagcat caggctcgac agcgatgaaa      720
caggcagtcg acaatgcata tgcaagaggg gttgtcgttg tagctgcagc agggaacagc     780
ggatcttcag gaaacacgaa tacaattggc tatcctgcga atacgattc tgtcatcgct      840
gttggtgcgg tagactctaa cagcaacaga gcttcatttt ccagtgtggg accagagctt     900
gaagtcatgg ctcctggcgc aggcgtatac agcacttacc caacgaacac ttatgcaaca     960
ttgagcggaa cgtcaatggc ttctcctcat gtagcgggag cagcagcttt gatcttgtca    1020
aaacatccga acctttcagc ttcacaagtc cgcaaccgtc tctccagcac ggcgacttat    1080
ttgggagact cctttctacta tgggaaaggt ctgatcaatg tcgaagctgc cgctcaataa   1140
```

<210> SEQ ID NO 16
<211> LENGTH: 1140
<212> TYPE: DNA
<213> ORGANISM: Artificial Sequence
<220> FEATURE:
<223> OTHER INFORMATION: Description of Artificial Sequence: Synthetic construct

<400> SEQUENCE: 16

```
atgatgagga aaagagtttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaggacat catcaaagag      180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
```

```
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg ggcgacaaca    660
aacggcatgg atgttatcaa tatgagcctt ggggagcat caggctcgac agcgatgaaa    720
caggcagtcg acaatgcata tgcaagaggg gttgtcgttg tagctgcagc agggaacagc    780
ggatcttcag gaaacacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgagcggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140
```

<210> SEQ ID NO 17
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 17

```
atgatgagga aaagagtttt ttggcttggg atgctgacgg ccttcatgct cgtgttcacg     60
atggcattca gcgattccgc ttctgctgct caaccggcga aaaatgttga aaaggattat    120
attgtcggat ttaagtcagg agtgaaaacc gcatctgtca aaaaggacat catcaaagag    180
agcggcggaa aagtggacaa gcagtttaga atcatcaacg cggcaaaagc gaagctagac    240
aaagaagcgc ttaaggaagt caaaaatgat ccggatgtcg cttatgtgga agaggatcat    300
gtggcccatg ccttggcgca aaccgttcct tacggcattc ctctcattaa agcggacaaa    360
gtgcaggctc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg ggcgacaaca    660
aacagcatgg atgttatcaa tatgagcctt ggggagcat caggctcgac agcgatgaaa    720
caggcagtcg acaatgcata tgcaagaggg gttgtcgttg tagctgcagc agggaacagc    780
ggatcttcag gatgcacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgagcggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140
```

<210> SEQ ID NO 18
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 18

```
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atgaggactt gaacgtagtc ggcggagcaa gctttgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt ggggagcat caggctcgac agcgatgaaa      720
caggcagtcg acaatgcata tgcaagaggg gttgtcgttg tagctgcagc agggaacagc     780
ggatcttcag gaaacacgaa tacaattggc tatcctgcga aatacgattc tgtcatcgct     840
gttggtgcgg tagactctaa cagcaacaga gcttcatttt ccagtgtggg accagagctt     900
gaagtcatgg ctcctggcgc aggcgtatac agcacttacc caacgaacac ttatgcaaca     960
ttgagcggaa cgtcaatggc ttctcctcat gtagcgggag cagcagcttt gatcttgtca    1020
aaacatccga acctttcagc ttcacaagtc cgcaaccgtc tctccagcac ggcgacttat    1080
ttgggagact ccttctacta tgggaaaggt ctgatcaatg tcgaagctgc cgctcaataa    1140
```

<210> SEQ ID NO 19
<211> LENGTH: 1085
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19

```
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt ggggagcat caggctcgac agcgatgaaa      720
```

```
caggcagtcg acaatgcata tgcaagaggg gttgtcgttg tagctgcagc agggaacagc    780
ggatcttcag gaaacacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgagcggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttggg                                                               1085

<210> SEQ ID NO 20
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 20
atgatgagga aaagagtttt ttggcttggg atgctgacgg ccttcatgct cgtgttcacg     60
atggcattca gcgattccgc ttctgctgct caaccggcga aaaatgttga aaaggattat    120
attgtcggat ttaagtcagg agtgaaaacc gcatctgtca aaaggacat catcaaagag     180 agcggcggaa aagtggacaa gcagtttaga atcatcaacg cggcaaaagc gaagctagac    240
aaagaagcgc ttaaggaagt caaaaatgat ccggatgtcg cttatgtgga agaggatcat    300
gtggcccatg ccttggcgca aaccgttcct tacggcattc ctctcattaa agcggacaaa    360
gtgcaggctc aaggctttaa gggagcgaat gtaaaagtag ccgtcctgga tacaggaatc    420
caagcttctc atgaggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg ggcgacaaca    660
aacggcatgg atgttatcaa tatgagcctt gggggagcat caggctcgac agcgatgaaa    720
caggcagtcg acaatgcata tgcaagaggg gttgtcgttg tagctgcagc agggaacagc    780
ggatcttcag gaaacacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgagcggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140

<210> SEQ ID NO 21
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
atgatgagga aaagagtttt ttggcttggg atgctgacgg ccttcatgct cgtgttcacg     60
atggcattca gcgattccgc ttctgctgct caaccggcga aaaatgttga aaaggattat    120
attgtcggat ttaagtcagg agtgaaaacc gcatctgtca aaaggacat catcaaagag     180
```

```
agcggcggaa aagtggacaa gcagtttaga atcatcaacg cggcaaaagc gaagctagac      240
aaagaagcgc ttaaggaagt caaaaatgat ccggatgtcg cttatgtgga agaggatcat      300
gtggcccatg ccttggcgca aaccgttcct tacggcattc ctctcattaa agcggacaaa      360
gtgcaggctc aaggctttaa gggagcgaat gtaaaagtag ccgtcctgga tacaggaatc      420
caagcttctc atccggactt gaacgtagtc ggcggagcaa gctttgtggc tggcgaagct      480
tataacaccg acggcaacgg acacggcaca catgttgccg gtacagtagc tgcgcttgac      540
aatacaacgg gtgtattagg cgttgcgcca agcgtatcct tgtacgcggt taaagtactg      600
aattcaagcg gaagcggatc atacagcggc attgtaagcg gaatcgagtg ggcgacaaca      660
aacggcatgg atgttatcaa tatgagcctt gggggagcat caggctcgac agcgatgaaa      720
caggcagtcg acaatgcata tgcaagaggg gttgtcgttg tagctgcagc agggaacagc      780
ggatcttcag gatgcacgaa tacaattggc tatcctgcga aatacgattc tgtcatcgct      840
gttggtgcgg tagactctaa cagcaacaga gcttcatttt ccagtgtggg agcagagctt      900
gaagtcatgg ctcctggcgc aggcgtatac agcacttacc caacgaacac ttatgcaaca      960
ttgagcggaa cgtcaatggc ttctcctcat gtagcgggag cagcagcttt gatcttgtca     1020
aaacatccga accctttcagc ttcacaagtc cgcaaccgtc tctccagcac ggcgacttat     1080
ttgggaagct ccttctacta tgggaaaggt ctgatcaatg tcgaagctgc cgctcaataa     1140
```

<210> SEQ ID NO 22
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22

```
atgatgagga aaaagagttt ttggcttggg atgctgacgg ccttcatgct cgtgttcacg       60
atggcattca gcgattccgc ttctgctgct caaccggcga aaaatgttga aaaggattat      120
attgtcggat ttaagtcagg agtgaaaacc gcatctgtca aaaaggacat catcaaagag      180
agcggcggaa aagtggacaa gcagtttaga atcatcaacg cggcaaaagc gaagctagac      240
aaagaagcgc ttaaggaagt caaaaatgat ccggatgtcg cttatgtgga agaggatcat      300
gtggcccatg ccttggcgca aaccgttcct tacggcattc ctctcattaa agcggacaaa      360
gtgcaggctc aaggctttaa gggagcgaat gtaaaagtag ccgtcctgga tacaggaatc      420
caagcttctc atgaggactt gaacgtagtc ggcggagcaa gctttgtggc tggcgaagct      480
tataacaccg acggcaacgg acacggcaca catgttgccg gtacagtagc tgcgcttgac      540
aatacaacgg gtgtattagg cgttgcgcca agcgtatcct tgtacgcggt taaagtactg      600
aattcaagcg gaagcggatc atacagcggc attgtaagcg gaatcgagtg ggcgacaaca      660
aacggcatgg atgttatcaa tatgagcctt gggggagcat caggctcgac agcgatgaaa      720
caggcagtcg acaatgcata tgcaagaggg gttgtcgttg tagctgcagc agggaacagc      780
ggatcttcag gaaacacgaa tacaattggc tatcctgcga aatacgattc tgtcatcgct      840
gttggtgcgg tagactctaa cagcaacaga gcttcatttt ccagtgtggg accagagctt      900
gaagtcatgg ctcctggcgc aggcgtatac agcacttacc caacgaacac ttatgcaaca      960
ttgaacggaa cgtcaatggc ttctcctcat gtagcgggag cagcagcttt gatcttgtca     1020
aaacatccga accctttcagc ttcacaagtc cgcaaccgtc tctccagcac ggcgacttat     1080
```
ttgggagact ccttctacta tgggaaaggt ctgatcaatg tcgaagctgc cgctcaataa    1140

<210> SEQ ID NO 23
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 23
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480
tataacaccg acggcaacgg acacggcaca catgttgccg gtacagtagc tgcgcttgac     540
aatacaacgg tgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt gggggagcat caggctcgac agcgatgaaa     720
caggcagtcg acaatgcata tgcaagaggg gttgtcgttg tagctgcagc agggaacagc     780
ggatcttcag gatgcacgaa tacaattggc tatcctgcga atacgattc tgtcatcgct     840 gttggtgcgg tagactctaa cagcaacaga gcttcatttt ccagtgtggg agcagagctt     900
gaagtcatgg ctcctggcgc aggcgtatac agcacttacc caacgaacac ttatgcaaca     960
ttgaacggaa cgtcaatggc ttctcctcat gtagcgggag cagcagcttt gatcttgtca    1020
aaacatccga accttttcagc ttcacaagtc cgcaaccgtc tctccagcac ggcgacttat    1080
ttgggaagct ccttctacta tgggaaaggt ctgatcaatg tcgaagctgc cgctcaataa    1140

<210> SEQ ID NO 24
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480

| | |
|---|---|
| tataacaccg acggcaacgg acacggcaca catgttgccg gtacagtagc tgcgcttgac | 540 |
| aatacaacgg gtgtattagg cgttgcgcca agcgtatcct tgtacgcggt taaagtactg | 600 |
| aattcaagcg gaagcggatc atacagcggc attgtaagcg gaatcgagtg ggcgacaaca | 660 |
| aacagcatgg atgttatcaa tatgagcctt gggggagcat caggctcgac agcgatgaaa | 720 |
| caggcagtcg acaatgcata tgcaagaggg gttgtcgttg tagctgcagc agggaacagc | 780 |
| ggatcttcag gatgcacgaa tacaattggc tatcctgcga aatacgattc tgtcatcgct | 840 |
| gttggtgcgg tagactctaa cagcaacaga gcttcatttt ccagtgtggg agcagagctt | 900 |
| gaagtcatgg ctcctggcgc aggcgtatac agcacttacc caacgaacac ttatgcaaca | 960 |
| ttgaacggaa cgtcaatggc ttctcctcat gtagcgggag cagcagcttt gatcttgtca | 1020 |
| aaacatccga acctttcagc ttcacaagtc cgcaaccgtc tctccagcac ggcgacttat | 1080 |
| ttgggaagct ccttctacta tgggaaaggt ctgatcaatg tcgaagctgc cgctcaataa | 1140 |

<210> SEQ ID NO 25
<211> LENGTH: 1140
<212> TYPE: DNA
<213> ORGANISM: Artificial Sequence
<220> FEATURE:
<223> OTHER INFORMATION: Description of Artificial Sequence: Synthetic construct

<400> SEQUENCE: 25

| | |
|---|---|
| atgatgagga aaagagtttt ttggcttggg atgctgacgg ccttcatgct cgtgttcacg | 60 |
| atggcattca gcgattccgc ttctgctgct caaccggcga aaaatgttga aaaggattat | 120 |
| attgtcggat ttaagtcagg agtgaaaacc gcatctgtca aaaaggacat catcaaagag | 180 |
| agcggcggaa aagtggacaa gcagtttaga atcatcaacg cggcaaaagc gaagctagac | 240 |
| aaagaagcgc ttaaggaagt caaaaatgat ccggatgtcg cttatgtgga agaggatcat | 300 |
| gtggcccatg ccttggcgca aaccgttcct tacggcattc ctctcattaa agcggacaaa | 360 |
| gtgcaggctc aaggctttaa gggagcgaat gtaaaagtag ccgtcctgga tacaggaatc | 420 |
| caagcttctc atccggactt gaacgtagtc ggcggagcaa gctttgtggc tggcgaagct | 480 |
| tataacaccg acggcaacgg acacggcaca catgttgccg gtacagtagc tgcgcttgac | 540 |
| aatacaacgg gtgtattagg cgttgcgcca agcgtatcct tgtacgcggt taaagtactg | 600 |
| aattcaagcg gaagcggatc atacagcggc attgtaagcg gaatcgagtg ggcgacaaca | 660 |
| aacagcatgg atgttatcta tatgagcctt gggggagcat caggctcgac agcgatgaaa | 720 |
| caggcagtcg acaatgcata tgcaagaggg gttgtcgttg tagctgcagc agggaacagc | 780 |
| ggatcttcag gaaacacgaa tacaattggc tatcctgcga aatacgattc tgtcatcgct | 840 |
| gttggtgcgg tagactctaa cagcaacaga gcttcatttt ccagtgtggg agcagagctt | 900 |
| gaagtcatgg ctcctggcgc aggcgtatac agcacttacc caacgaacac ttatgcaaca | 960 |
| ttgaacggaa cgtcaatggc ttctcctcat gtagcgggag cagcagcttt gatcttgtca | 1020 |
| aaacatccga acctttcagc ttcacaagtc cgcaaccgtc tctccagcac ggcgacttat | 1080 |
| ttgggaagct ccttctacta tgggaaaggt ctgatcaatg tcgaagctgc cgctcaataa | 1140 |

<210> SEQ ID NO 26
<211> LENGTH: 1140
<212> TYPE: DNA
<213> ORGANISM: Artificial Sequence
<220> FEATURE:
<223> OTHER INFORMATION: Description of Artificial Sequence: Synthetic construct

<400> SEQUENCE: 26

```
atgatgagga aaaagagttt ttggcttggg atgctgacgg ccttcatgct cgtgttcacg      60
atggcattca gcgattccgc ttctgctgct caaccggcga aaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt gggggagcat caggctcgac agcgatgaaa     720
caggcagtcg acaatgcata tgcaagaggg gttgtcgttg tagctgcagc agggaacagc     780
ggatcttcag gatgcacgaa tacaattcgc tatcctgcga aatacgattc tgtcatcgct     840
gttggtgcgg tagactctaa cagcaacaga gcttcatttt ccagtgtggg agcagagctt     900
gaagtcatgg ctcctggcgc aggcgtatac agcacttacc caacgaacac ttatgcaaca     960
ttgaacggaa cgtcaatggc ttctcctcat gtagcgggag cagcagcttt gatcttgtca    1020
aaacatccga accttcagc ttcacaagtc cgcaaccgtc tctccagcac ggcgacttat    1080
ttgggaagct ccttctacta tgggaaaggt ctgatcaatg tcgaagctgc cgctcaataa    1140
```

<210> SEQ ID NO 27
<211> LENGTH: 1140
<212> TYPE: DNA
<213> ORGANISM: Artificial Sequence
<220> FEATURE:
<223> OTHER INFORMATION: Description of Artificial Sequence: Synthetic construct

<400> SEQUENCE: 27

```
atgatgagga aaaagagttt ttggcttggg atgctgacgg ccttcatgct cgtgttcacg      60
atggcattca gcgattccgc ttctgctgct caaccggcga aaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atgaggactt gaacgtagtc ggcggagcaa gctttgtggc tggcgaagct     480
tataacaccg acggcaacgg acacggcaca catgttgccg gtacagtagc tgcgcttgac     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt gggggagcat caggctcgac agcgatgaaa     720
caggcagtcg acaatgcata tgcaagaggg gttgtcgttg tagctgcagc agggaacagc     780
ggatcttcag gaaacacgaa tacaattggc tatcctgcga aatacgattc tgtcatcgct     840
```

```
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggagact ccttctacta tgggaaaggt ctgatcaatg tcgaagctgc cgctcaataa   1140
```

<210> SEQ ID NO 28
<211> LENGTH: 1140
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 28

```
atgatgagga aaaagagttt ttggcttggg atgctgacgg ccttcatgct cgtgttcacg     60
atggcattca gcgattccgc ttctgctgct caaccggcga aaaatgttga aaaggattat    120
attgtcggat ttaagtcagg agtgaaaacc gcatctgtca aaaaggacat catcaaagag    180
agcggcggaa agtggacaa gcagtttaga atcatcaacg cggcaaaagc gaagctagac    240
aaagaagcgc ttaaggaagt caaaaatgat ccggatgtcg cttatgtgga gaggatcat    300 gtggcccatg cctggcgca aaccgttcct acggcattc ctctcattaa gcggacaaa    360 gtgcaggctc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttgac    540
aatacaacgg gtgtattagg cgttgcgcca agcgtatcct tgtacgcggt taaagtactg    600
aattcaagcg gaagcggatc atacagcggc attgtaagcg gaatcgagtg gcgacaaca    660 aacagcatg atgttatcta tatgagcctt gggggagcat caggctcgac agcgatgaaa    720
caggcagtcg acaatgcata tgcaagaggg gttgtcgttg tagctgcagc agggaacagc    780
ggatcttcag gatgcacgaa tacaattggc tatcctgcga aatacgattc tgtcatcgct    840
gttggtgcgg tagactctaa cagcaacaga gcttcatttt ccagtgtggg accagagctt    900
gaagtcatgg ctcctggcgc aggcgtatac agcacttacc caacgaacac ttatgcaaca    960
ttgaacggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140
```

<210> SEQ ID NO 29
<211> LENGTH: 379
<212> TYPE: PRT
<213> ORGANISM: Bacillus licheniformis

<400> SEQUENCE: 29

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60
```

```
Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Val Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Gln
370                 375
```

THERMOSTABLE PROTEASE AND METHODS OF MAKING AND USING THE SAME

CROSS REFERENCE TO RELATED APPLICATIONS

This application is a continuation of International application no. PCT/US2017/029628, filed on Apr. 26, 2017, which claims the benefit of U.S. Provisional Patent Application No. 62/328,051, filed Apr. 27, 2016, the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Aug. 26, 2020, is named 341_10_UTTL_SL.txt and is 73,755 bytes in size.

FIELD OF INVENTION

The presently disclosed subject matter relates generally to thermostable variants of kerA protease derived from *Bacillus licheniformis*. The presently disclosed subject matter further relates to DNA encoding the disclosed proteases, nucleic acid constructs, vectors, and host cells comprising the polynucleotides, as well as methods of their production and use.

BACKGROUND

Enzymes are commonly used as additives in animal feed to improve digestibility, thereby making the feed more efficient and increasing its energy content. Specifically, protease enzymes aid in protein digestion as they hydrolyze the less digestible proteins and break them down into more usable peptides. However, the heat treatment of animal feeds during processing poses a significant challenge for the development and use of proteases as feed supplements. In typical feed pelleting processes, the feed is preconditioned at temperatures of about 70° C. to 80° C., followed by pelleting at temperatures in the range of 80° C. to 85° C. Due to the increased temperatures, enzymes will often irreversibly lose their enzymatic activity. Thus, it would be beneficial to provide enzymes having improved thermostability during processing conditions.

SUMMARY

In some embodiments, the presently disclosed subject matter is directed to a polypeptide variant of *Bacillus licheniformis* kerA protease comprising a sequence as set forth in (a) A298P:N322S:S363D (SEQ ID NO: 1), N322S (SEQ ID NO: 2), G222S: N265C: N322S (SEQ ID NO: 3), P145E: A298P: N322S: S363D (SEQ ID NO: 4), N322S: S363D (SEQ ID NO: 5), P145E: N322S (SEQ ID NO: 6), N265C: N322S (SEQ ID NO: 7), P145E: A298P:S363D (SEQ ID NO: 8), N265C (SEQ ID NO: 9), G222S:N265C (SEQ ID NO: 10), G222S: N227Y (SEQ ID NO: 11), N265C: G270R (SEQ ID NO: 12), P145E: S363D (SEQ ID NO: 13), or G222S: N227Y: N265C: A298P (SEQ ID NO: 14); (b) the variant sequence as set forth in part (a) and having at least 70% sequence identity in a remainder of the sequence, wherein the variant sequence has protease activity and retains enhanced thermostability relative to *Bacillus licheniformis* kerA protease; (c) the variant sequence as set forth in part (b), wherein the at least 70% sequence identity consists of only conservative substitutions; or (d) a fragment of the variant sequence as set forth in parts (a), (b), or (c), wherein the fragment has protease activity and retains enhanced thermostability relative to *Bacillus licheniformis* kerA protease.

In some embodiments, polynucleotides are provided encoding the variant proteases.

In some embodiments, nucleic acid constructs or expression vectors are provided comprising the polynucleotides encoding the variant proteases, wherein the polynucleotides are operably linked to one or more control sequences that direct the production of the variant proteases in an expression host cell.

In some embodiments, recombinant expression host cells are provided comprising the polynucleotides encoding the variant proteases, wherein the polynucleotides are operably linked to one or more control sequences that direct the production of the variant proteases.

In some embodiments, a method is provided of producing the variant proteases, comprising cultivating a recombinant expression host cell comprising a polynucleotide encoding the variant protease, wherein the polynucleotide is operably linked to one or more control sequences that direct the production of the variant protease under conditions conducive for production of the variant protease.

In some embodiments, an animal feed is provided comprising the variant protease, wherein the variant protease is present in an amount sufficient to enhance the digestibility of the feed by an animal.

In some embodiments, an animal feed additive is provided comprising the variant protease.

DETAILED DESCRIPTION

Figure 1:
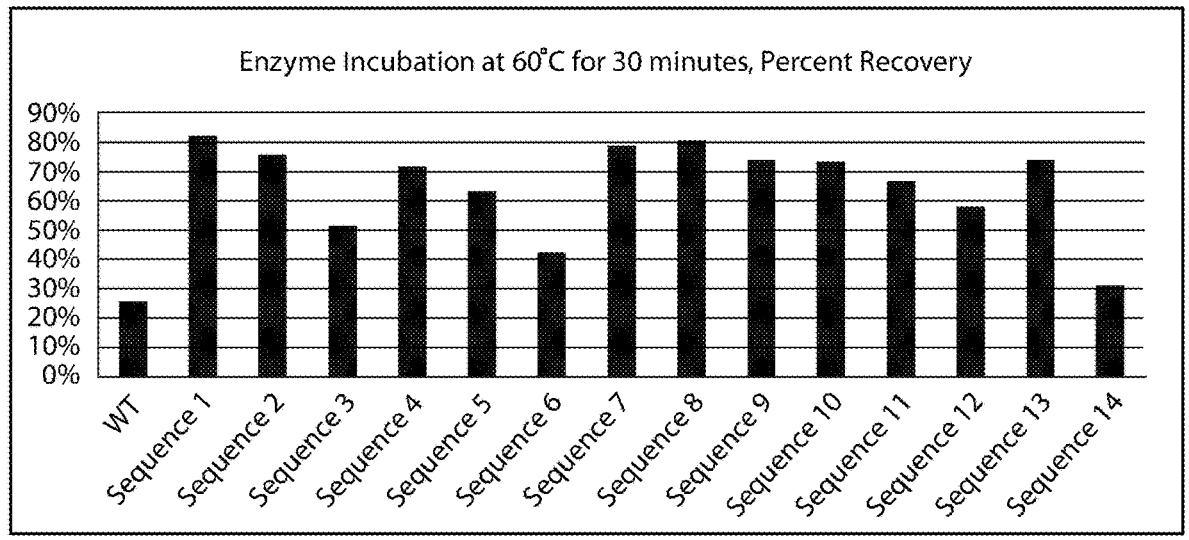
FIG. 1 is a bar graph showing the percent recovery of activity of wild type *Bacillus licheniformis* kerA protease Accession No. 053521 ("kerA") and kerA variants after incubation at 60° C. for 30 minutes according to one or more embodiments of the presently disclosed subject matter.

The presently disclosed subject matter now will be described more fully hereinafter with reference to the accompanying Figures, in which some (but not all) embodiments are shown. Many modifications and other embodiments of the presently disclosed subject matter set forth herein will come to mind to one skilled in the art having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter relates to variants of kerA protease derived from *Bacillus licheniformis* (i.e., *Bacillus licheniformis* kerA protease Accession No. Q53521 ("kerA") having increased thermostability). The thermostable variants each have at least one modified amino acid and some variants have up to four modifications in the amino acid sequence as compared to the wild type kerA enzyme. The modified amino acid(s) result in variants with enhanced stability to heat, low pH, or both. The presently disclosed subject matter further relates to DNA encoding the disclosed protease variants, nucleic acid constructs, expression vectors, and host cells comprising the polynucleotides, as well as to methods of their production and use. In some embodiments, the presently disclosed subject matter relates to use of the variant proteases as animal feed additives to improve the digestibility and/or the nutritional value of the feed.

Unless otherwise defined, all technical terms used herein have the same meaning as commonly understood by one of ordinary skill in the art to which this disclosure belongs.

Following long-standing patent law convention, the terms "a," "an," and "the" refer to one or more when used in this application, including the claims. Thus, for example, reference to "a protein" includes a plurality of proteins, unless the context clearly is to the contrary.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

As used herein, the term "feed" refers to any compound, preparation, mixture, or composition suitable for or intended for intake by an animal. In some embodiments, the feed can comprise a poultry feed or swine feed composition.

The term "nucleic acid construct" or "expression vector" refers to a linear or circular DNA molecule that comprises a polynucleotide encoding a ker variant operably linked to additional nucleotides that provide for expression of the variant kerA protease.

The term "improved thermostability" or "enhanced thermostability" or "increased themostability" as used herein refers to a variant displaying increased retention of protease activity after a period of incubation at elevated temperatures (60° C. to 85° C. for 20 seconds to 30 minutes in some embodiments) relative to the wild type kerA or increased activity at low pH (pH 4 in some embodiments), either in a buffer or under conditions such as those that exist during product storage/transport or conditions similar to those that exist during industrial use. Whether or not a disclosed variant protease has an improved thermostability as compared to a wild type kerA protease can be determined as described in the Examples. In addition, the terms "stability" and "thermostability" are herein used interchangeably for the purposes of the specification and claims.

The terms "isolated" and "purified" are herein used interchangeably for the purposes of the specification and claims and as used herein refer to a material that is removed from its original environment (e.g., the natural environment if it is naturally occurring). For example, a material is said to be "purified" when it is present in a particular composition in a higher or lower concentration than exists in a naturally occurring or wild type organism or in combination with components not normally present upon expression from a naturally occurring or wild type organism. Thus, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still be isolated in that such vector or composition is not part of its natural environment. In some embodiments, a nucleic acid or protein is said to be purified if it gives rise to essentially one band in an electrophoretic gel or blot.

As used herein, the term "protease" refers to any protease enzyme and the terms "protease" and "enzyme" are herein used interchangeably for the purposes of the specification and claims. Thus, in some embodiments, the protease is of a type of protease that is used in the agricultural industry as an animal feed additive to improve the digestibility of the feed.

As used herein, the term "protein" includes proteins, polypeptides, and peptides. In some embodiments, the terms "protein", "polypeptide" and "peptide" can be used interchangeably.

The term "sequence identity" as used herein refers to the relatedness between two amino acid sequences or between two nucleotide sequences. For purposes of the presently disclosed subject matter, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277). In some embodiments, the optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows: (Identical Residues.times.100)/(Length of Alignment-Total Number of Gaps in Alignment).

The term "stability" as used herein refers to the ability of a protease variant to have equal or greater activity compared to the wild type under standard conditions, and an increased ability to retain activity after exposure to increased temperatures and/or acidic conditions (about pH 4.0) for 30 minutes. In some embodiments, the term "stability" can be used interchangeably with the term "thermostability".

The term "variant" as used herein refers to a polypeptide having protease activity comprising an alteration (i.e., a substitution, insertion, and/or deletion) at one or more positions compared to the wild type (a protease having the identical amino acid sequence of said variant but not having the alterations at one or more of said specified positions). A substitution means a replacement of an amino acid occupying a position with a different amino acid; a deletion means removal of an amino acid occupying a position; and an insertion means the addition of one or more amino acids. In some embodiments, the disclosed variant sequence comprises at least one alteration and the remainder of the sequence is at least 70% identical to the amino acids set forth in SEQ ID NO: 1. Thus, in some embodiments, the remainder sequences of the disclosed variants are at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% identity to SEQ ID NO: 1.

The term "wild type" or "wild type protease" or "wild type kerA" or "kerA" as used herein refers to *Bacillus licheniformis* PWD-1 protease kerA Accession No. Q53521. The sequence for the wild type protease is set forth in SEQ ID NO: 29.

The presently disclosed subject matter relates to proteolytic enzyme kerA variants that exhibit improved thermal stability relative to the wild type protease. As set forth in Table 1, the disclosed protease variants were derived by the mutation of at least one amino acid residue of the mature *Bacillus licheniformis* PWD-1 protease kerA ("kerA").

As would be appreciated by those of ordinary skill in the art, in Table 1 below the amino acid represented by A is Alanine, P is Proline, N is asparagine, S is serine, D is aspartic acid, G is glycine, C is cysteine, E is glutamic acid, Y is tyrosine, and R is arginine. Similarly, in Table 1 the DNA base represented by A is adenine, T is thymine, G is guanine, and C is cytosine. For the amino acid substitutions in Table 1, the following nomenclature is used: original amino acid, position, substituted amino acid. Accordingly, the substitution of alanine with proline at position 298 in the wild type kerA amino acid sequence is designated as "A298P".

TABLE 1 kerA Protease Variant Amino Acid and DNA Sequence Changes

| ID | Amino Acid Change (DNA Base Change) | Corresponding Amino Acid Sequence SEQ ID NO | Corresponding DNA Base Sequence SEQ ID NO |
|---|---|---|---|
| Variant 1 | A298P (G892C) N322S (A965G) S363D (A1087G, G1088A) | SEQ ID NO: 1 | SEQ ID NO: 15 |
| Variant 2 | N322S (A965G) | SEQ ID NO: 2 | SEQ ID NO: 16 |
| Variant 3 | G222S (G664A) N265C (A793T, A794G) N322S (A965G) | SEQ ID NO: 3 | SEQ ID NO: 17 |
| Variant 4 | P145E (C433G, C434A) A298PG(G892C) N322S (A965G) S363D (A1087G, G1088A) | SEQ ID NO: 4 | SEQ ID NO: 18 |
| Variant 5 | N322S (A965G) S363D (A1078G, G1088A) | SEQ ID NO: 5 | SEQ ID NO: 19 |
| Variant 6 | P145E (C433G, C434A) N322S (A965G) | SEQ ID NO: 6 | SEQ ID NO: 20 |
| Variant 7 | N265C (A793T, A794G) N322S (A965G) | SEQ ID NO: 7 | SEQ ID NO: 21 |
| Variant 8 | P145E (C433G, C434A) A298P (G892C) S363D (A1087G, G1088A) | SEQ ID NO: 8 | SEQ ID NO: 22 |
| Variant 9 | N265C (A793T, A794G) | SEQ ID NO: 9 | SEQ ID NO: 23 |
| Variant 10 | G222S (G664A) N265C (A793T, A794G) | SEQ ID NO: 10 | SEQ ID NO: 24 |
| Variant 11 | G222S (G664A) N227Y (A679T) | SEQ ID NO: 11 | SEQ ID NO: 25 |
| Variant 12 | N265C (A793T, A794G) G270R (G808C) | SEQ ID NO: 12 | SEQ ID NO: 26 |
| Variant 13 | P145E (C433G, C434A) S363D (A1087G, G1088A) | SEQ ID NO: 13 | SEQ ID NO: 27 |
| Variant 14 | G222S (G664A) N227Y (A679T) N265C (A793T, A794G) A298P (G892C) | SEQ ID NO: 14 | SEQ ID NO: 28 |

The disclosed variants comprise an amino acid modification in at least one position corresponding to positions 145, 222, 227, 265, 270, 298, 322, and/or 363 of the mature wild type kerA protease. As would be understood by those of ordinary skill in the art, the disclosed variants can optionally further comprise one or more additional alterations at one or more other positions. The amino acid changes can be of a minor nature (conservative amino acid substitutions or insertions that do not significantly affect the folding and/or activity of the protein), small deletions (typically of 1-30 amino acids), small amino- or carboxyl-terminal extensions (such as an amino-terminal methionine residue), small linker peptides of up to 20-25 residues, and/or small extensions that facilitate purification by changing net charge or another function (such as a poly-histidine tract, an antigenic epitope, and/or a binding domain).

Thus, in some embodiments, a variant protease of the present disclosure can have one or more substitutions in amino acid residues in addition to the modifications allowing for the enhanced thermostability. These one or more substitutions can be conservative or non-conservative substitutions, but in either case, the variant proteases having the additional substitutions have substantial protease activity and retain enhanced thermostability relative to the wild type enzyme. Examples of conservative substitutions include the substitution of one non-polar (hydrophobic) residue such as alanine, isoleucine, valine, leucine, or methionine for another; the substitution between asparagine and glutamine, the substitution of one large aromatic residue such as tryptophan, tyrosine, or phenylalanine for another; the substitution of one small polar (hydrophilic) residue for another such as between glycine, threonine, serine, and proline; the substitution of one basic residue such as lysine, arginine, or histidine for another; or the substitution of one acidic residue such as aspartic acid or glutamic acid for another.

The presently disclosed subject matter can also include a fragment of the variant sequences set forth herein, so long as the fragment has protease activity and retains enhanced thermostability relative to the wild type kerA protease.

The disclosed variants exhibit increased thermostability (i.e., are more stable than wild type kerA wild-type protease) at high temperature conditions, such as (but not limited to) temperatures of about 60° C. to about 85° C. Whether or not a variant protease has improved thermostability as compared to wild type protease can be determined as described in the Examples.

In some embodiments, the presently disclosed subject matter is directed to a polypeptide variant of *Bacillus licheniformis* kerA protease comprising a sequence as set forth in (a) A298P: N322S: S363D (SEQ ID NO: 1), N322S (SEQ ID NO: 2), G222S: N265C: N322S (SEQ ID NO: 3), P145E: A298P: N322S: S363D (SEQ ID NO: 4), N322S: S363D (SEQ ID NO: 5), P145E: N322S (SEQ ID NO: 6), N265C: N322S (SEQ ID NO: 7), P145E: A298P: S363D (SEQ ID NO: 8), N265C (SEQ ID NO: 9), G222S:N265C (SEQ ID NO: 10), G222S:N227Y (SEQ ID NO: 11), N265C: G270R (SEQ ID NO: 12), P145E: S363D (SEQ ID NO: 13), or G222S: N227Y: N265C: A298P (SEQ ID NO: 14); (b) the variant sequence as set forth in part (a) and having at least 70% sequence identity in a remainder of the sequence, wherein the variant sequence has protease activity and retains enhanced thermostability relative to *Bacillus licheniformis* kerA protease; (c) the variant sequence as set forth in part (b), wherein the at least 70% sequence identity consists of only conservative substitutions; or (d) a fragment of the variant sequence as set forth in parts (a), (b), or (c), wherein the fragment has protease activity and retains enhanced thermostability relative to *Bacillus licheniformis* kerA protease. In some embodiments, the at least 70% sequence identity comprises at least 85% identity, at least 90% identity, at least 95% identity, at least 98% identity, or at least 99% identity.

In some embodiments, polynucleotides are provided encoding the variant proteases. In some embodiments, a nucleic acid construct or an expression vector is provided comprising the polynucleotide encoding the variant protease, wherein the polynucleotide is operably linked to one or more control sequences that direct the production of the variant protease in an expression host cell.

In some embodiments, a recombinant expression host cell is provided comprising a polynucleotide encoding the variant protease, wherein the polynucleotide is operably linked to one or more control sequences that direct the production of the variant protease.

In some embodiments, a method is provided for producing the variant protease of the present disclosure, the method comprising cultivating a recombinant expression host cell comprising a polynucleotide encoding the variant protease, wherein the polynucleotide is operably linked to one or more control sequences that direct the production of the variant protease under conditions conducive for production of the variant protease. The method can further include recovering the variant protease.

In some embodiments, a whole broth formulation or cell culture composition is provided comprising the variant protease of the present disclosure.

The presently disclosed subject matter also relates to methods for obtaining the disclosed kerA variants. In some embodiments, the disclosed method comprises providing a wild type kerA protease, introducing a substitution of the wild type kerA at amino acid position 145, 222, 227, 265, 270, 298, 322, 363, or combinations thereof, and recovering the variant. The wild type protease from which the disclosed protease variants are derived is a kerA protease obtained from *Bacillus licheniformis*. In some embodiments, the kerA gene can be obtained by isolating the chromosomal DNA from the *B. licheniformis* wild type strain, constructing DNA probes having homology to putative DNA sequences encoding regions of the kerA protease, preparing genomic libraries from the isolated chromosomal DNA, and screening the libraries for the gene of interest by hybridization to the probes.

The kerA variants can be prepared using any mutagenesis procedure known in the art, including (but not limited to) site-directed mutagenesis, synthetic gene construction, semi-synthetic gene construction, random mutagenesis, shuffling, and the like. Thus, in some embodiments, the disclosed variants can be prepared using site-directed mutagenesis of the wild type kerA gene accomplished in vitro by PCR involving the use of oligonucleotide primers containing the desired mutation. In some embodiments, site-directed mutagenesis can also be accomplished in vivo by methods known in the art. However, it should be understood that the disclosed method is not limited.

In some embodiments, variants of kerA can be generated with a pool of primers specific to the targeted mutations to create a library of kerA mutants with a range of mutation combinations. In some embodiments, the library can be generated with the kerA gene cloned on an expression plasmid. The expression plasmid can be any plasmid that can be subjected to recombinant DNA procedures, and the choice of plasmid can depend on the host cell into which it is to be introduced. After site-directed mutagenesis, the plasmid pool can be transformed into *E. coli*. The plasmid pool can then be isolated from *E. coli* and transformed into *B. subtilis*. Individual clones can then be expressed and assayed for protease activity after exposure to increasing temperature and/or acidic pH. Positive clones can be sequenced to identify the mutation combinations for each clone.

It should be understood that in addition to the variant kerA proteases discussed herein, the presently disclosed subject matter also comprises polynucleotides encoding the variant kerA proteases. The presently disclosed subject matter further comprises nucleic acid constructs and/or expression vectors comprising the disclosed polynucleotides, wherein the polynucleotides are operably linked to one or more control sequences that direct the production of the variant proteases in host expression cells. Recombinant expression host cells comprising recombinant polynucleotides that encode variant proteases are also included within the scope of the presently disclosed subject matter.

In some embodiments, the disclosed protease variants can be purified using any of the wide variety of methods known and used in the art. For example, the variants can be purified using chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, and/or extraction.

In some embodiments, the presently disclosed subject matter is directed to a method of producing the disclosed variant proteases. Particularly, the disclosed method comprises cultivating a recombinant expression host cell comprising a polynucleotide encoding a variant protease, wherein the polynucleotide is operably linked to one or more control sequences that direct the production of the variant protease under conditions conducive for production of the variant protease. In some embodiments, the disclosed method further comprises recovering the variant protease. In some embodiments, the presently disclosed subject matter includes a whole broth formulation or cell culture composition comprising the variant proteases.

In some embodiments, an animal feed additive is provided comprising the variant protease of the present disclosure.

The presently disclosed subject matter further relates to compositions (such as animal feed compositions) comprising a disclosed kerA variant protease. In some embodiments, the variant protease is present in an amount sufficient to enhance the digestibility of the animal feed by an animal. In some embodiments, the animal feed comprising the disclosed kerA variant protease is a poultry or a swine feed. The disclosed compositions can be prepared in accordance with methods known in the art and can be in the form of a liquid or a dry composition. For instance, the composition comprising the kerA variants can be in the form of granulates or microgranulates. The polypeptide to be included in the composition can be stabilized in accordance with methods known in the art. Thus, in some embodiments, the disclosed kerA variants can be added directly to animal feed compositions or can be used in the production of one or more intermediate animal feed compositions, such as feed additives or premixes that are subsequently added to the feed or used in a treatment process. The variant protease can be present in the composition in an amount sufficient to enhance the digestibility of the feed by an animal. In some embodiments, the disclosed variants can be used in conjunction with a nutritionally acceptable carrier, a nutritionally acceptable diluent, a nutritionally acceptable excipient, a nutritionally acceptable adjuvant, and/or a nutritionally active ingredient. In some embodiments, the disclosed composition or additive can comprise a fat-soluble vitamin, a water-soluble vitamin, a trace mineral, or combinations thereof.

In some embodiments, the disclosed protease variants can be present in the composition in an amount of about 6 to about 3,000 units of protease activity per gram of feed (i.e, 6 U/g to about 3,000 U/g feed). One unit of protease activity (U) is defined as the change in absorbance at a wavelength of 410 nm of 0.01 at 37° C., pH 8.0, in 15 minutes. Thus, in some embodiments, the feed can comprise about 6-3,000; about 10-2,000; or about 12-1,500 U/g feed of protease variants.

In some embodiments, the disclosed compositions can be used with feeds selected from the group comprising a) cereals, such as small grains (e.g., wheat, barley, rye, oats and combinations thereof) and/or large grains such as maize or sorghum; b) byproducts of cereals, such as corn gluten meal, distillers dried grain solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

The presently disclosed subject matter provides protease variants that exhibit increased thermostability at increased temperatures. Thus, when the variants are included as part of an animal feed composition, an increased amount of protease survives the feed processing cycle. As a result, the nutritional capacity of the feed compositions is improved.

EXAMPLES

Example 1

Identification of *Bacillus licheniformis* kerA Variants with Enhanced Stability The objective was to identify amino acid sequence positions on *Bacillus licheniformis* kerA protease Accession No. 053521 ("kerA") that would have the greatest influence on its thermal stability and stability under acidic conditions. Potential amino acid substitutions were identified through a thorough literature search of previously engineered proteases. Three protein sequences were chosen from the literature. The sequences were aligned, and based on this alignment potential hot spots were identified after avoiding positions that had the possibility of affecting catalysis. The proposed mutations that were identified include P145E, S363D from *Bacillus gibsonii* alkaline protease in Martinez et al., *Biotechnology & Bioengineering*, Vol. 110, No. 3, 2013; N227Y from *Bacillus licheniformis* BBE11-1 in Liu et al., *World Journal of Microbiology and Biotechnology*, 2013, Vol. 29, No. 29, pp. 825-832; and G222S, N265C, G270R, A298P, N322S in Subtilisin E from Zhao et al., *Protein Engineering*, Vol. 12, No. 1, 1999, pp. 47-53.

Variants of kerA were generated randomly with a pool of primers specific to the targeted mutations to create a library of kerA mutants with a range of mutation combinations. The library was generated with the kerA gene cloned on a *B. subtilis* expression plasmid (pRB374). Post-PCR (site-directed mutagenesis standard protocols were used), the plasmid pool was transformed into *E. coli*. The plasmid pool was then isolated from *E. coli* and transformed into *B. subtilis*. Subsequently, individual clones were expressed and assayed for protease activity in a high throughput manner.

Positive mutants were identified as having equal to or greater than wild type protease activity under standard conditions, and an increased ability to retain activity after exposure to increasing temperature and/or acidic pH (4.0), for 30 minutes. The positive clones identified were sequenced to identify the one or more mutations for each clone. In total, 14 kerA variants were identified as having positive properties with regard to thermostability. The specific amino acid and DNA base changes are shown in Table I herein above.

For the activity measurement, the expressed variant proteases were incubated at 60° C. for 30 minutes, with a replicate held at room temperature. Percent recovery was calculated by comparing each variant's ability to retain activity. The data is represented graphically in FIG. 1. The wild type kerA enzyme retains about 26% protease activity post high temperature incubation. All of the kerA variants were shown to retain 30-82% activity, a marked improvement compared to the wild type enzyme.

The amino acid and nucleotide sequences for each of the 14 kerA variants are listed above in Table 1.

Example 2

Activity Testing of *Bacillus licheniformis* kerA Variants at pH 4

Figure 2:
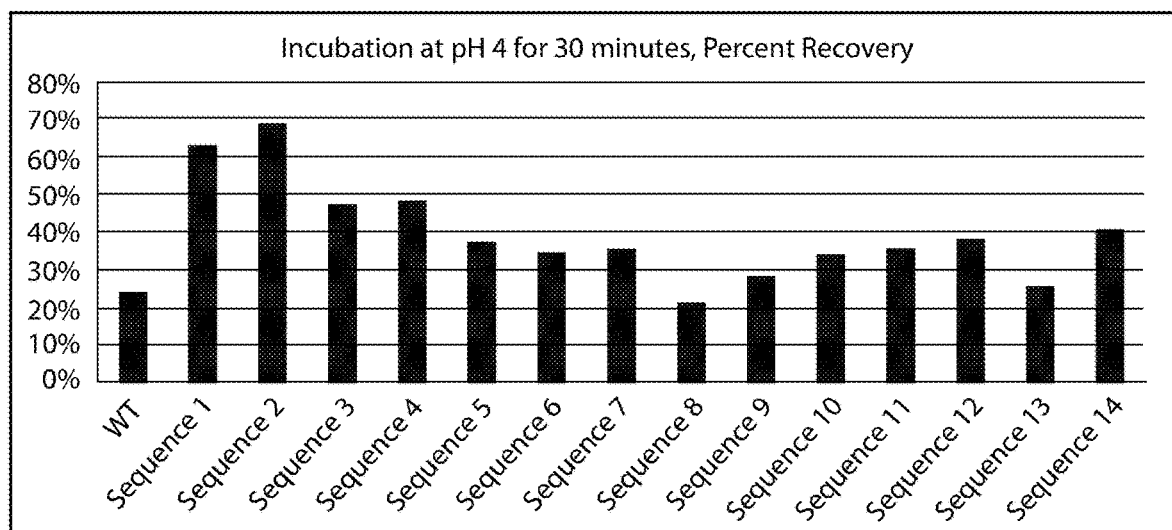
FIG. 2 is a bar graph illustrating the percent recovery of activity of wild type kerA protease and kerA variants after incubation at pH 4 for 30 minutes according to one or more embodiments of the presently disclosed subject matter.

Variants 1-14 and the wild type kerA enzyme were incubated at room temperature at pH 4.0 for 30 minutes. The percent activity remaining after the 30 minute incubation was measured and is shown in FIG. 2. As illustrated in FIG. 2, the wild type kerA enzyme retains about 24% protease activity after the incubation at pH 4. Each of kerA variants tested retained greater activity than the wild type enzyme (about 25-69% activity) with the exception of the Variant 8, which only retained about 20% activity.

Example 3

Feed Mill Conditioning Environment Study

Figure 3:
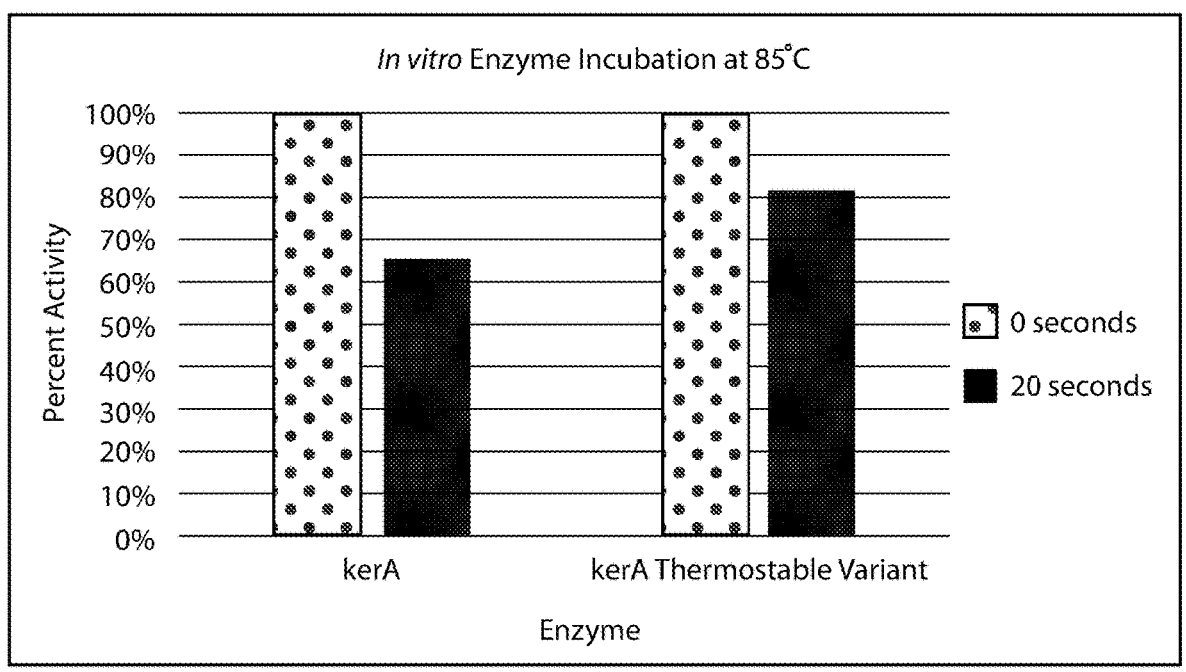
FIG. 3 is a bar graph illustrating percent activity of wild type kerA protease and kerA Variant 1 after in vitro incubation at 85° C. for 20 seconds according to one or more embodiments of the presently disclosed subject matter.

Both wild type kerA and a Variant 1 were incubated at 85° C. in buffer to simulate pellet mill conditions. After incubation, both samples were assayed for protease activity under standard conditions. The data are shown graphically in FIG. 3. The kerA sample retained 65% of its initial activity after a 20 second incubation. The Variant 1 sample retained 82% of its activity after a 20 second incubation, representing a 23% increase in thermal stability under the testing conditions. Both samples were also assayed for protease activity after no incubation (control). In the control assay, both samples showed 100% activity.

Example 4

Feed Mill Pelleting Study

Figure 4:
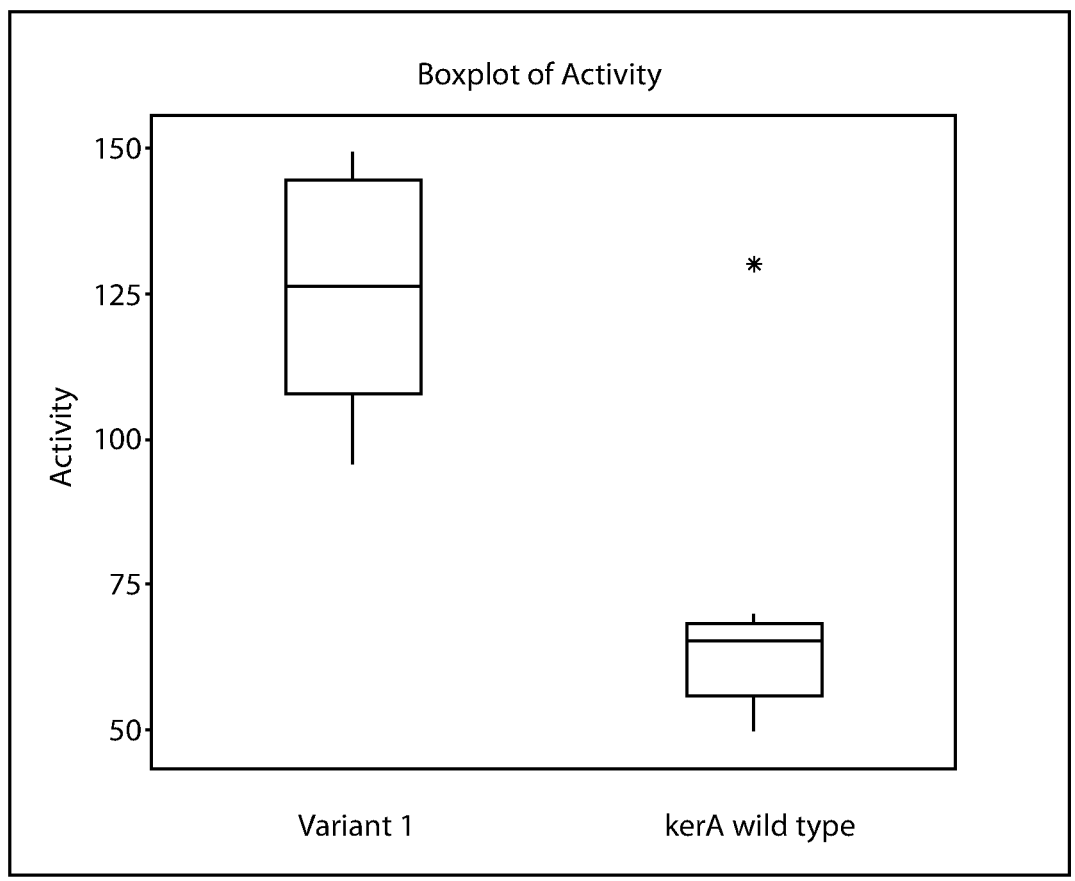
FIG. 4 is a boxplot illustrating percent activity of wild type kerA protease and kerA Variant 1 after undergoing pelleting conditions according to one or more embodiments of the presently disclosed subject matter.

A high-temperature pelleting study was performed to confirm the increased thermal stability of kerA thermal stable variant enzyme compared to wild type kerA. Two corn-soy-based broiler diets, one with kerA enzyme and the second with kerA thermostable variant (Variant 1) were mixed as mash and pelleted in a 1 ton/hour pellet mill with target conditioning temperature of 90° C. (195° F.). The target conditioning time was 35 seconds with a production rate of about 1 ton per hour, 60 RPM, and a die size of 5/32" with a 1.25" effective thickness. After pelleting, both samples were assayed for protease activity under standard conditions. A graph of activity is shown in FIG. 4. An 80% increase in post-pellet recovery of Variant 1 compared to wild type kerA was seen under these conditions.

What is claimed is:

1. A polypeptide variant of a sequence of *Bacillus licheniformis* kerA protease as set forth in SEQ ID NO: 29, the variant protease comprising a sequence as set forth in:
   a. i) SEQ ID NO: 1,
      ii) SEQ ID NO: 2,
      iii) SEQ ID NO: 3,
      iv) SEQ ID NO: 4,
      v) SEQ ID NO: 5,
      vi) SEQ ID NO: 6,
      vii) SEQ ID NO: 7,
      viii) SEQ ID NO: 8,
      ix) SEQ ID NO: 9,
      x) SEQ ID NO: 10,
      xi) SEQ ID NO: 12, or
      xii) SEQ ID NO: 13;
   b. i) the variant protease SEQ ID NO: 1, which has the following amino acid modifications A298P: N322S: S363D, and optionally has further modifications in addition to A298P: N322S: S363D, wherein SEQ ID NO: 1 with optional further modifications in addition to A298P: N322S: S363D has at least 70% sequence identity to SEQ ID NO: 29,
      ii) the variant protease of SEQ ID NO: 2, which has the following amino acid modification N322S, and optionally has further modifications in addition to N322S, wherein SEQ ID NO: 2 with optional further modifications in addition to N322S has at least 70% sequence identity to SEQ ID NO: 29, iii) the variant protease of SEQ ID NO: 3, which has the following amino acid modifications G222S: N265C: N322S, and optionally has further modifications in addition to G222S: N265C: N322S, wherein SEQ ID NO: 3 with optional further modifications in addition to G222S: N265C: N322S has at least 70% sequence identity to SEQ ID NO: 29;

iv) the variant protease of SEQ ID NO: 4, which has the following amino acid modifications P145E: A298P: N322S: S363D, and optionally has further modifications in addition to P145E: A298P: N322S: S363D, wherein SEQ ID NO: 4 with optional further modifications in addition to P145E: A298P: N322S: S363D has at least 70% sequence identity to SEQ ID NO: 29;

v) the variant protease of SEQ ID NO: 5, which has the following amino acid modifications N322S: S363D, and optionally has further modifications in addition to N322S: S363D, wherein SEQ ID NO: 5 with optional further modifications in addition to N322S: S363D has at least 70% sequence identity to SEQ ID NO: 29;

vi) the variant protease of SEQ ID NO: 6, which has the following amino acid modifications P145E: N322S, and optionally has further modifications in addition to P145E: N322S, wherein SEQ ID NO: 6 with optional further modifications in addition to P145E: N322S has at least 70% sequence identity to SEQ ID NO: 29;

vii) the variant protease of SEQ ID NO: 7, which has the following amino acid modifications N265C: N322S, and optionally has further modifications in addition to N265C: N322S, wherein SEQ ID NO: 7 with optional further modifications in addition to N265C: N322S has at least 70% sequence identity to SEQ ID NO: 29;

viii) the variant protease of SEQ ID NO: 8, which has the following amino acid modifications P145E: A298P: S363D, and optionally has further modifications in addition to P145E: A298P: S363D, wherein SEQ ID NO: 8 with optional further modifications in addition to P145E: A298P: S363D has at least 70% sequence identity to SEQ ID NO: 29;

ix) the variant protease of SEQ ID NO: 9, which has the following amino acid modification N265C, and optionally has further modifications in addition to N265C, wherein SEQ ID NO: 9 with optional further modifications in addition to N265C has at least 70% sequence identity to SEQ ID NO: 29;

x) the variant protease of SEQ ID NO: 10, which has the following amino acid modifications G222S: N265C, and optionally has further modifications in addition to G222S: N265C, wherein SEQ ID NO: 10 with optional further modifications in addition to G222S: N265C has at least 70% sequence identity to SEQ ID NO: 29;

xi) the variant protease of SEQ ID NO: 12, which has the following amino acid modifications N265C: G270R, and optionally has further modifications in addition to N265C: G270R, wherein SEQ ID NO: 12 with optional further modifications in addition to N265C: G270R has at least 70% sequence identity to SEQ ID NO: 29; or xii) the variant protease of SEQ ID NO: 13, which has the following amino acid modifications P145E: S363D, and optionally has further modifications in addition to P145E: S363D, wherein SEQ ID NO: 13 with optional further modifications in addition to P145E: S363D has at least 80% sequence identity to SEQ ID NO: 29, wherein the variant protease has protease activity and retains enhanced thermostability relative to SEQ ID NO: 29; or c. any of the variant proteases as set forth in part (b)(i) through (b)(xii), wherein the modifications consist of only conservative substitutions.

2. The variant protease of claim 1, wherein the at least 70% sequence identity comprises at least 90% identity.

3. A polynucleotide encoding the variant protease of claim 1.

4. A nucleic acid construct or expression vector comprising the polynucleotide of claim 3, wherein the polynucleotide is operably linked to one or more control sequences that direct the production of the variant protease in an expression host cell.

5. A recombinant expression host cell comprising a polynucleotide encoding the variant protease of claim 1, wherein the polynucleotide is operably linked to one or more control sequences that direct the production of the variant protease.

6. A method of producing the variant protease of claim 1, comprising cultivating a recombinant expression host cell comprising a polynucleotide encoding the variant protease of claim 1, wherein the polynucleotide is operably linked to one or more control sequences that direct the production of the variant protease under conditions conducive for production of the variant protease.

7. The method of claim 6, further comprising recovering the variant protease.

8. A whole broth formulation or cell culture composition comprising the variant protease of claim 1.

9. An animal feed comprising the variant protease of claim 1, wherein the variant protease is present in an amount sufficient to enhance the digestibility of the feed by an animal.

10. The animal feed of claim 9, wherein the amount ranges from 6,000 to 3,000,000 U/kg of feed.

11. The method of claim 10, wherein the animal feed is a poultry or a swine feed.

12. An animal feed additive comprising the variant protease of claim 1.

13. The animal feed additive of claim 12, further comprising one or more of a fat-soluble vitamin, a water-soluble vitamin, or a trace mineral, and combinations thereof.

14. A method for improving the nutritional value of an animal feed, comprising adding the variant protease of claim 1 to the animal feed.

15. The method of claim 14, wherein the animal feed is a poultry or a swine feed.

16. A polypeptide variant of a sequence of *Bacillus licheniformis* kerA protease as set forth in SEQ ID NO: 29, the variant protease comprising an amino acid modification in at least one position corresponding to positions 145, 222, 265, 270, 298, 322, and/or 363 of the protease of SEQ ID NO: 29 and having at least 90% sequence identity to SEQ ID NO: 29, wherein the variant sequence has protease activity and retains enhanced thermostability relative to the *Bacillus licheniformis* kerA protease of SEQ ID NO: 29.

17. The polypeptide variant of claim 16 comprising an amino acid modification in at least two positions corresponding to positions 145, 222, 265, 270, 298, 322, and/or 363 of the *Bacillus licheniformis* kerA protease of SEQ ID NO: 29.

18. The polypeptide variant of claim 16 comprising an amino acid modification in at least three positions corresponding to positions 145, 222, 265, 270, 298, 322, and/or 363 of the *Bacillus licheniformis* kerA protease of SEQ ID NO: 29.

19. The polypeptide variant of claim 16, wherein the amino acid modification is a conservative substitution.

20. A polypeptide variant of a sequence of *Bacillus licheniformis* kerA protease as set forth in SEQ ID NO: 29, the variant protease comprising an amino acid modification in at least one position corresponding to positions 145, 222, 265, 298, 322, and/or 363 of the protease of SEQ ID NO: 29 and having at least 90% sequence identity to SEQ ID NO: 29, wherein the variant sequence retains at or above 70% protease activity after incubation at high temperature conditions relative to the *Bacillus licheniformis* kerA protease of SEQ ID NO: 29.

21. The polypeptide variant of claim 20, wherein high temperature conditions comprise temperatures of about 60° C. to about 85° C.

22. The polypeptide variant of claim 20, wherein the variant sequence also retains at or above 60% protease activity after incubation at low pH relative to the *Bacillus licheniformis* kerA protease of SEQ ID NO: 29.

\* \* \* \* \*